United States Patent [19]
Puritch et al.

[11] Patent Number: 4,870,102
[45] Date of Patent: Sep. 26, 1989

[54] MITICIDAL COMPOSITION

[75] Inventors: George S. Puritch, Saanichton; Michelle D. Gorman, Victoria, both of Canada

[73] Assignee: Safer, Inc., Newton, Mass.

[21] Appl. No.: 182,137

[22] Filed: Apr. 15, 1988

[51] Int. Cl.$^4$ ............................................. A01N 55/04
[52] U.S. Cl. ..................................... 514/493; 514/560
[58] Field of Search ................................ 514/493, 560

[56] References Cited
U.S. PATENT DOCUMENTS
3,657,451  4/1972  Horne .................................. 514/493

OTHER PUBLICATIONS
Merck Manual, pp. 570–571, "Fenbutatin Oxide."

Primary Examiner—Leonard Schenkman
Attorney, Agent, or Firm—Lahive & Cockfield

[57] ABSTRACT

A composition and method for killing or controlling mites by contacting them with a mixture of certain organo-tin compounds, preferably tri-(2-methyl-2-phenylpropyl) tin hydroxide, and a salt of a fatty acid, primarily sodium or potassium fatty acid soaps. The components of the composition interact to yield a miticidal activity greater than the activities of the components used separately. The composition has fewer long-term environmental effects than occur with the organo-tin compound used alone.

6 Claims, No Drawings

MITICIDAL COMPOSITION

BACKGROUND OF THE INVENTION

This invention relates to a composition and method for controlling infestations of mites. More particularly, the invention relates to a synergistic blend of certain known insecticidally active components which effect such control much more efficiently, and does so with less environmental risk.

U.S. Pat. No. 3,657,451 discloses a composition that is effective in controlling mites. The composition is an organo-tin compound of the formula:

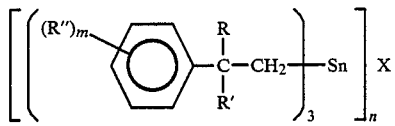

wherein R is a lower alkyl, R' and R" are each hydrogen or lower alkyl, m is an integer from 0 to 2, n is 1 or 2, and X is a member of the group consisting of halogen, $OH^-$ and $RCOO^-$ when n is 1, and $-O-$ when n is 2. An embodiment of this class of compounds is sold by Shell Oil Company under the trademark "Vendex". Vendex is di[tri-(2-methyl-2-phenylpropyl)tin]-oxide, i.e., the compound set forth above where R and R' are methyl, m is 0, n is 2, and X is $-O-$. Upon dissolution in water, the oxide linkage is hydrolyzed to produce tri-(2-methyl-2-phenyl propyl)tin hydroxide.

Aqueous solutions of salts of certain fatty acids, primarily sodium or potassium fatty acid soaps, have recently come into use as insecticides, and have moderate effectiveness against mites. The salts are naturally occurring materials having no known long term environmental effects. Such a composition is presently sold by Safer, Inc., of Wellesley, Mass., under the trademark "Insecticidal Soap".

It was hypothesized that such fatty acid soaps might be used to extend the efficacy of organo-tin compounds as both the Vendex and the Insecticidal Soap might each retain insecticidal activity in admixture, and might form a stable complex soluton. If both materials retained efficacy in such a composition, it might be possible to reduce the amount of organo tin compound required to control mites in a given area and thus to provide an environmentally more compatible miticide.

It is an object of this invention to provide a miticide that includes an appreciable quantity of material that is not harmful to the environment and that is unexpectedly effective.

This and other objects and features of the invention will be apparent from the description and the claims that follow.

SUMMARY OF THE INVENTION

It has now been discovered that the combination of miticidally active organo-tin compounds with miticidally active fatty acid soaps can provide a composition with miticidal effectiveness that is superior to either of the elements of the combination alone. That is, the compositions have a miticidal effect greater than the expected, additive effects of the separate components.

The invention features an aqueous mixture of (1) an organo-tin compound, preferably tri-(2-methyl-2-phenylpropyl) tin hydroxide or chloride, e.g., the water soluble form of Vendex, and (2) a mixture of salts of a fatty acid, preferably a sodium or potassium fatty acid soap, more preferably a mixture of monocarboxylic acids and their salts having between 15 and 18 carbon atoms, and most preferably a mixture of oleic acid and its alkali metal salts and linoleic acid and its alkali metal salts. The fatty acid component may comprise other monocarboxylic acids or their salts having less than 21 carbon atoms. Particularly preferred is a mixture comprising from about 50% to about 80% by weight of oleic acid, 5% to 30% by weight of linoleic acid (or their salts), and the balance comprising no more than about 20% by weight of a mixture of saturated fatty acid salt, for example, the salts or acid form of palmitic acid and stearic acid.

The composition may be manufactured by mixing solid organo-tin compound powder with water, and then adding and mixing the wetted powder to Insecticidal Soap. In Insecticidal Soap may be in concentrated or ready-to-use form, e.g., may comprise a 40% by weight fatty acid soap solution (50% fatty acids, a major amount of which is in alkali metal, preferably potassium form), or this composition diluted with water. The monocarboxylic acid mixture most preferably comprises at least 70 percent oleic acid and its alkali metal salt and at least 6 percent linoleic acid and its alkali metal salt. The remaining components of the carboxylic acid mixture, if any, comprises other monocarboxylic acids (or their salts) having less than 21 carbon atoms or other inert materials.

Aqueous mixtures in which 1.0 part by weight hexakis (2-methyl-2-phenylpropyl) distannoxane (Vendex) which converts to the hydroxide form when mixed with water, are combined with 1–200 parts fatty acids are preferred. More preferred are compositions wherein the insecticidal soap: organo-tin weight ratios are 3:1 to 100:1, and most preferred is 10:1 to 50:1. The composition is effective on application to a plant at a dilution in a liquid such that the applied solution contains at least about 25 ppm of the organo-tin compound.

DESCRIPTION OF THE INVENTION

The insecticide of the invention comprises a mixture of two insecticidally effective materials. One is an organo-tin compound having the general formula:

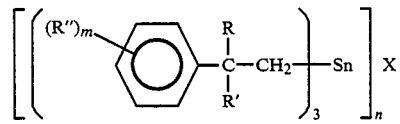

wherein R is a lower alkyl, R' and R" are each hydrogen or lower alkyl, m is an integer from 0 to 2, n 1 or 2, and X is a member of the group consisting of halogen, $OH^-$ and $RCOO^-$ when n is 1, and $-O-$ when n is 2. Such materials can be produced as disclosed in U.S. Pat. No. 3,657,451, the disclosure of which is incorporated herein by reference.

The currently preferred compound is the hydroxide of tri-(2-methyl-2-phenyl propyl) tin, i.e., the structure defined above when R and R' are methyl, m is 0, n is 1, and X is $OH^-$. This compound is produced when Vendex, a commercially available miticide (Shell Oil Co.), is mixed with water.

The other material is a solution of an insecticidally active salt of fatty acids, primarily sodium or potassium fatty acid soaps. Preferably, the material is a mixture of monocarboxylic acids and their salts having between 15 and 18 carbon atoms, such as oleic acid and its alkali metal salt, and linoleic acid and its alkali metal salt. There may be other components of the composition comprising monocarboxylic acids or their salts having less than 21 carbon atoms.

Particularly preferred is a mixture of salts that contains from about 50 to about 80% by weight of oleic acid and 5% to 30% by weight of linoleic acid, the balance being a small amount (at most 20% by weight) of other fatty acid materials, for example, palmitic and stearic acids or their salts.

A suitable solution is available commercially from Safer, Inc. of Wellesley, Mass. under the trademark "Insecticidal Soap". The composition of this product varies slightly from batch to batch, but always includes at least about 70% salt (or acid form) oleic acid, and at least about 6% salt (or acid form) linoleic acid. The remainder of the solutes comprise other fatty acids or salts having between 12 and 20 carbon atoms.

The fatty acid soap is desirable as a "spreader sticker" to be used in conjunction with the organo-tin compound, i.e., aids in diluting appropriately the oragno tin miticide and delivering and adhering it to the surface to be protected. Furthermore, the combination of the fatty acid soap and the organo-tin compound turns out to have a miticidal effectiveness greater than the sum of their individual effectiveness, thereby created an enhanced miticide that is much less harmful to the environment than the organo-tin compound used alone.

To produce the composition, the organo-tin miticide is mixed with water to form a wet powder, and the powder is then mixed with an aqueous solution of the fatty acids. Preferably, at least about 3 to 50 parts fatty acid should be present per part organo-tin compound. Compositions comprising other ratios of the active ingredients may be used, but the advantage and object of diminishing the amount of organo-tin introduced into the environment are defeated as the amount of organo-tin compound composition is increased.

The compositions are applied to the surface to be protected, e.g., the leaves and fruit of a plant, using, for example, a conventional spray device. Best results are achieved for a given composition when the dilution in water is set such that the organo-tin component is present at a level of at least 25 ppm. Generally, dilutions in which the organo-tin compound is present at levels greater than about 150 ppm result in product waste.

In order to more fully demonstrate the invention, the following non-limiting examples are given. The compositions in all cases were made as set forth above using the commercially available miticide Vendex and mixing with commercially available Insecticidal Soap in amounts sufficient to achieve the various weight ratios and absolute concentrations of ingredients set forth.

EXAMPLE 1

The efficacy of "Insecticidal Soap" solution and "Vendex" solution alone and in combination on *Tetrachynus urticae* (Two spotted spider mites) was analyzed.

Eighteen three month old, staked cucumber plants (v. Marketer) were infested with *T. urticae* for 1 month. Two plants were randomly assigned to each of nine possible treatments:

(1) control (tap water)
(2) 1000 ppm ai "Insecticidal Soap" solution (wt/wt)
(3) 5000 ppm ai "Insecticidal Soap" solution (wt/wt)
(4) 25 ppm "Vendex" compound (wt/v)
(5) 75 ppm "Vendex" compound (wt/v)
(6) 5000 ppm ai "Insecticidal Soap" and 25 ppm "Vendex" (wt/wt) (200:1)
(7) 5000 ppm ai "Insecticidal Soap" and 75 ppm "Vendex" (wt/wt) (66:1)
(8) 1000 ppm ai "Insecticidal Soap" and 25 ppm "Vendex" (wt/wt) (40:1)
(9) 1000 ppm ai "Insecticidal Soap" and 75 ppm "Vendex" (wt/wt) (13:1)

Both sides of the leaves were sprayed with a 10 cc. plastic disposable syringe, fitted to accommodate a furnace burner tip (Monarch .75 GPH 45 AR)- to the point of wetting. The plants were then randomly placed on a bench top and left for 16 hours before assessment. Assessment was done by removing, one leaf at a time, the three uppermost leaves of the plant, then punching out two circles of leaf (4.15 cm$^2$) and assessing the number of dead mites against the total number of mites on each. The data appear in Table 1.

TABLE 1

% Mortality of two-spotted mites, *Tetranychus urticare* to treatment solutions.

| TREATMENT COMPOSITION (wt. ratio IS:Vendex) | % MORTALITY ON LEAF: 1 | 2 | 3 | AVG. % MORT. | ABBOTS CORRECTED MORT. % |
|---|---|---|---|---|---|
| 1. Control (water) | 9.5 | 11.4 | 16.7 | 11.8 | 0 |
|  | 13.8 | 8.0 | 11.8 |  |  |
| 2. .1% "Insecticidal Soap" | 17.1 | 16.7 | 14.3 | 24.5 | 14.3 |
|  | 16.7 | 44.4 | 37.5 |  |  |
| 3. .5% "IS" | 75 | 76.9 | 80.0 | 80.9 | 78.3 |
|  | 83.3 | 87.0 | 83.0 |  |  |
| 4. 25 ppm "Vendex" | 16.7 | 18.6 | 16.7 | 17.2 | 6.1 |
|  | 20.0 | 13.8 | 17.6 |  |  |
| 5. 75 ppm "Vendex" | 17.0 | 16.7 | 19.5 | 22.2 | 11.8 |
|  | 28.5 | 23.1 | 28.6 |  |  |
| 6. .1% "IS" + 75 ppm "Vendex" (13:1) | 88.9 | 84.2 | 50.0 | 61.1 | 57.0 |
|  | 60.8 | 50.0 | 38.6 |  |  |
| 7. .5% "IS" + 75 ppm "Vendex" (66:1) | 96.7 | 86.2 | 100.0 | 94.9 | 94.2 |
|  | 95.8 | 100 | 90.6 |  |  |
| 8. .1% "IS" + 25 ppm "Vendex" (40:1) | 65.2 | 81.8 | 44.7 | 60.5 | 55.2 |
|  | 76.9 | 50.0 | 81.8 | 44.1 |  |
| 9. .5% "IS" + 25 ppm "Vendex" (200:1) | 93.7 | 91.8 | 97.6 | 92.1 | 91.0 |
|  | 92.8 | 89.5 | 87.0 |  |  |

A synergistic miticidal effect was observed in each of the combinations, indicating that the "Insecticidal Soap" solution unexpectedly improves the miticidal effectiveness of the "Vendex" solution. As is illustrated by the data in the more statistically significant percentage mortality in the Abbotts corrected findings, the expected, additive mortalities for runs 6-9 using compositions embodying the composition of the invention would be, respectively, (14.3+11.8) 26.1%, (78.3+11.8) 90.1%, (14.3+6.1) 20.4%, and (78.2+6.1) 84.4%, whereas the observed mortalities were 57.0%, 94.2%, 55.2%, and 91.0%.

EXAMPLE 2

The efficacy of the "Insecticidal Soap" and "Vendex" solutions were tested alone and in combination for the control of the two-spotted pider mite, *T. urticae*, using the conventional backpack sprayer commonly used in greenhouse operations.

Thirty-nine, five week old cucumber plants, (v. Marketer), were infested with *T. urticae* for 1 week. Nine plants were randomly assigned to each of the following four treatments in aqueous solutions. Three other plants were not treated.

1. 5000 ppm ai "Insecticidal Soap" (wt/wt)
2. 25 ppm "Vendex" (wt/wt)
3. 5000 ppm ai "Insecticidal Soap"+25 ppm "Vendex" (200:1 wt/wt)
4. Control-tap water Plants and mites were then sprayed with a 10 L Sanex backpack sprayer (45° Core, D4 Cone) to both sides of the leaves to the point of wetting. After spraying, the plants were placed randomly on a bench top and assessed 24 hours later.

Assessment involved removing, one at a time, the three uppermost leaves of the plants, punching out a circle of leaf (4.15 cm$^2$), and counting the total number of living and dead mites. The results appear in Table 2.

TABLE 2

% Mortality of two-spotted mites, *Tetranychus urticae* to treatment solutions.

| TREAT-MENT | % MORTALITY ON LEAF: 1 | 2 | 3 | MEAN MORT. (%) | AVG. % MORT. | ABBOTTS CORRECTED MORT. (%) |
|---|---|---|---|---|---|---|
| Control | 25.0 | 8.0 | 6.6 | 13.2 | | |
| | 27.3 | 7.4 | 21.9 | 18.9 | | |
| | 33.3 | 31.8 | 20.0 | 28.4 | | |
| | 25.0 | 34.1 | 21.7 | 26.9 | | |
| | 17.4 | 5.9 | 28.6 | 17.3 | 19.8 | 0.0 |
| | 12.5 | 11.8 | 16.7 | 13.7 | | |
| | 16.7 | 25.0 | 32.6 | 24.8 | | |
| | 7.9 | 15.0 | 22.7 | 15.2 | | |
| | 23.5 | 17.6 | 18.2 | 19.8 | | |
| Control Untreated | 30.0 | 23.1 | 25.0 | 26.0 | | |
| | 0.0 | 20.0 | 30.0 | 25.0 | 23.1 | 4.1 |
| | 16.7 | 20.0 | 18.2 | 18.3 | | |
| 25 ppm "Vendex" | 37.5 | 27.8 | 33.3 | 32.9 | | |
| | 23.1 | 53.8 | 20.0 | 32.3 | | |
| | 22.2 | 20.0 | 27.3 | 23.2 | | |
| | 18.2 | 23.5 | 25.0 | 22.2 | | |
| | 40.0 | 23.1 | 33.3 | 28.6 | 26.1 | 7.9 |
| | 24.2 | 23.5 | 22.2 | 23.3 | | |
| | 27.3 | 13.6 | 20.0 | 20.3 | | |
| | 27.9 | 32.0 | 28.1 | 29.3 | | |
| | 26.1 | 9.0 | 33.3 | 22.8 | | |
| 5000 ppm "IS" | 70.0 | 91.0 | 55.6 | 72.2 | | |
| | 77.7 | 77.7 | 100.0 | 85.1 | | |
| | 82.9 | 85.4 | 100.0 | 89.4 | | |
| | 55.6 | 70.4 | 100.0 | 75.3 | | |
| | 53.8 | 35.3 | 46.2 | 45.1 | 78.3 | 72.9 |
| | 81.8 | 86.1 | 71.4 | 79.8 | | |
| | 95.2 | 91.5 | 75.0 | 87.2 | | |
| | 100.0 | 96.8 | 84.2 | 93.7 | | |
| | 55.6 | 87.5 | 87.0 | 76.7 | | |
| 5000 ppm "IS" + 25 ppm "Vendex" | 11.0 | 90.9 | 80.0 | 85.5 | | |
| | 100.0 | 94.3 | 100.0 | 98.1 | | |
| | 93.2 | 96.6 | 28.3 | 72.7 | | |
| | 90.3 | 78.6 | 100.0 | 95.4 | 91.1 | 88.9 |
| | 93.3 | 78.6 | 100.0 | 90.6 | | |
| | 95.2 | 83.3 | 90.0 | 89.5 | | |
| | 95.0 | 96.1 | 92.9 | 94.7 | | |
| | 97.3 | 100.0 | 92.9 | 96.7 | | |
| | 90.9 | 100.0 | 100.0 | 97.0 | | |

As illustrated by the data, the organo-tin compound used alone at a concentration of 25 ppm produced a 7.9% mortality; the Insecticidal soap used alone at a concentration of 5000 ppm produced a 72.9 percent mortality. Yet, together, the observed coverage percent mortality was 88.9%, i.e., greater than the expected additive mortality of 80.8%.

The invention may be embodied in other specific forms.

What is claimed is:

1. A miticidal composition for controlling and retarding mite infestation, said composition consisting essentially of an aqueous solution containing a miticidally effective amount of a combination of:
   (A) An insecticidal soap containing a mixture of monocarboxylic acids and the alkali metal salts thereof having between 15 and 18 carbon atoms including oleic acid or its alkali metal salts, and
   (B) one or a mixture of

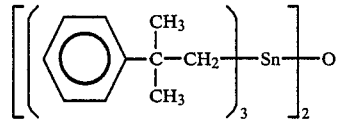

and the weight ratio of components A:B is between 100:1 and 1:1.

2. The composition of claim 1 wherein component A comprises
   at least 70 percent oleic acid and its alkali metal salts and at least 6 percent lineoleic acid and its alkali metal salts.

3. The composition of claim 1 wherein component (B) comprises at least about 25 ppm by weight of said solution.

4. The composition of claim 1 wherein the weight ratio A:B is 100:1 to 3:1.

5. The composition of claim 1 wherein the weight ratio A:B is 50:1 to 10:1.

6. The method of controlling mite infestation on a plant comprising the step of applying the composition of any of claims 1, 2, 3, 4 and 5 to surfaces of the plant in an amount and at a concentration sufficient to kill a substantial fraction of mites infesting said plant.

* * * * *

UNITED STATES PATENT AND TRADEMARK OFFICE
CERTIFICATE OF CORRECTION

PATENT NO. : 4,870,102

DATED : September 26, 1989

INVENTOR(S) : Puritch et al.

It is certified that error appears in the above-identified patent and that said Letters Patent is hereby corrected as shown below:

Column 6, line 43, before the word "and" insert -- and

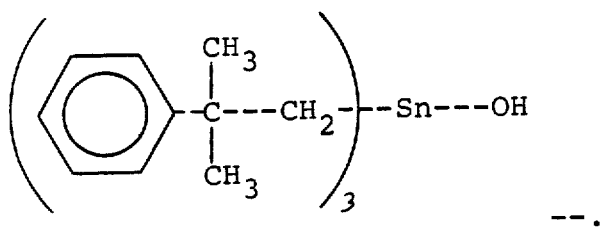

--.

Signed and Sealed this

Twenty-fifth Day of September, 1990

*Attest:*

HARRY F. MANBECK, JR.

*Attesting Officer*     *Commissioner of Patents and Trademarks*